United States Patent [19]
Tanner, II

[11] Patent Number: 5,540,667
[45] Date of Patent: Jul. 30, 1996

[54] NEEDLE GUARD ASSEMBLY FOR SYRINGE

[75] Inventor: John C. Tanner, II, Lake Bluff, Ill.

[73] Assignee: Abbott Laboratories, Abbott Park, Ill.

[21] Appl. No.: 384,635

[22] Filed: Feb. 6, 1995

Related U.S. Application Data

[63] Continuation of Ser. No. 276,880, Jul. 18, 1994, abandoned, which is a continuation of Ser. No. 55,058, Apr. 19, 1993, abandoned, which is a continuation of Ser. No. 765,356, Sep. 25, 1991, abandoned.

[51] Int. Cl.$^6$ .................................................. A61M 5/32
[52] U.S. Cl. ............................ 604/192; 604/82; 604/198; 604/263
[58] Field of Search .................................. 604/82, 83, 86, 604/110, 167, 171, 197–199, 218, 236, 240, 263, 283, 411–414, 905, 195; 128/919

[56] References Cited

U.S. PATENT DOCUMENTS

| | | | |
|---|---|---|---|
| 3,826,261 | 7/1974 | Killinger et al. | 128/26 |
| 3,889,673 | 6/1975 | Dovey et al. | 604/192 |
| 4,116,196 | 9/1978 | Kaplan et al. | 604/192 |
| 4,148,316 | 4/1979 | Xanthopoulos | 604/199 |
| 4,576,211 | 3/1986 | Valentini et al. | 604/905 |
| 4,681,567 | 7/1987 | Masters et al. | 604/198 |
| 4,752,292 | 6/1988 | Lopez et al. | 604/905 |
| 4,834,716 | 5/1989 | Ogle, II | 604/192 |
| 4,850,970 | 7/1989 | Sutherland | 604/192 |
| 4,872,552 | 10/1989 | Unger | 604/192 |
| 4,897,083 | 1/1990 | Martell | 604/192 |
| 4,909,290 | 3/1990 | Coccia | 604/905 |
| 4,932,940 | 6/1990 | Walker et al. | 604/110 |
| 4,950,260 | 8/1990 | Bonaldo | 604/905 |
| 4,958,622 | 9/1990 | Selenke | 604/192 |
| 4,998,925 | 3/1991 | Al-Sioufi et al. | 604/905 |
| 5,147,324 | 9/1992 | Skakoon et al. | 604/192 |
| 5,151,090 | 9/1992 | Best et al. | 604/192 |
| 5,195,992 | 3/1993 | Dudar et al. | 604/192 |

*Primary Examiner*—C. Fred Rosenbaum
*Assistant Examiner*—Mark Bockelman
*Attorney, Agent, or Firm*—Michael J. Ward

[57] ABSTRACT

A needle guard assembly for a prefilled emergency syringe includes a cylindrical sidewall which extends coaxially with the syringe needle. The sidewall is joined to the syringe housing by spin welding or sonic welding an annular fusible portion that extends axially rearward from an annular flange on the base of the sidewall to contact the front wall of the housing. The sidewall is joined to the housing so that an annular clearance space for the hood is maintained between the hub and the sidewall guard.

11 Claims, 1 Drawing Sheet

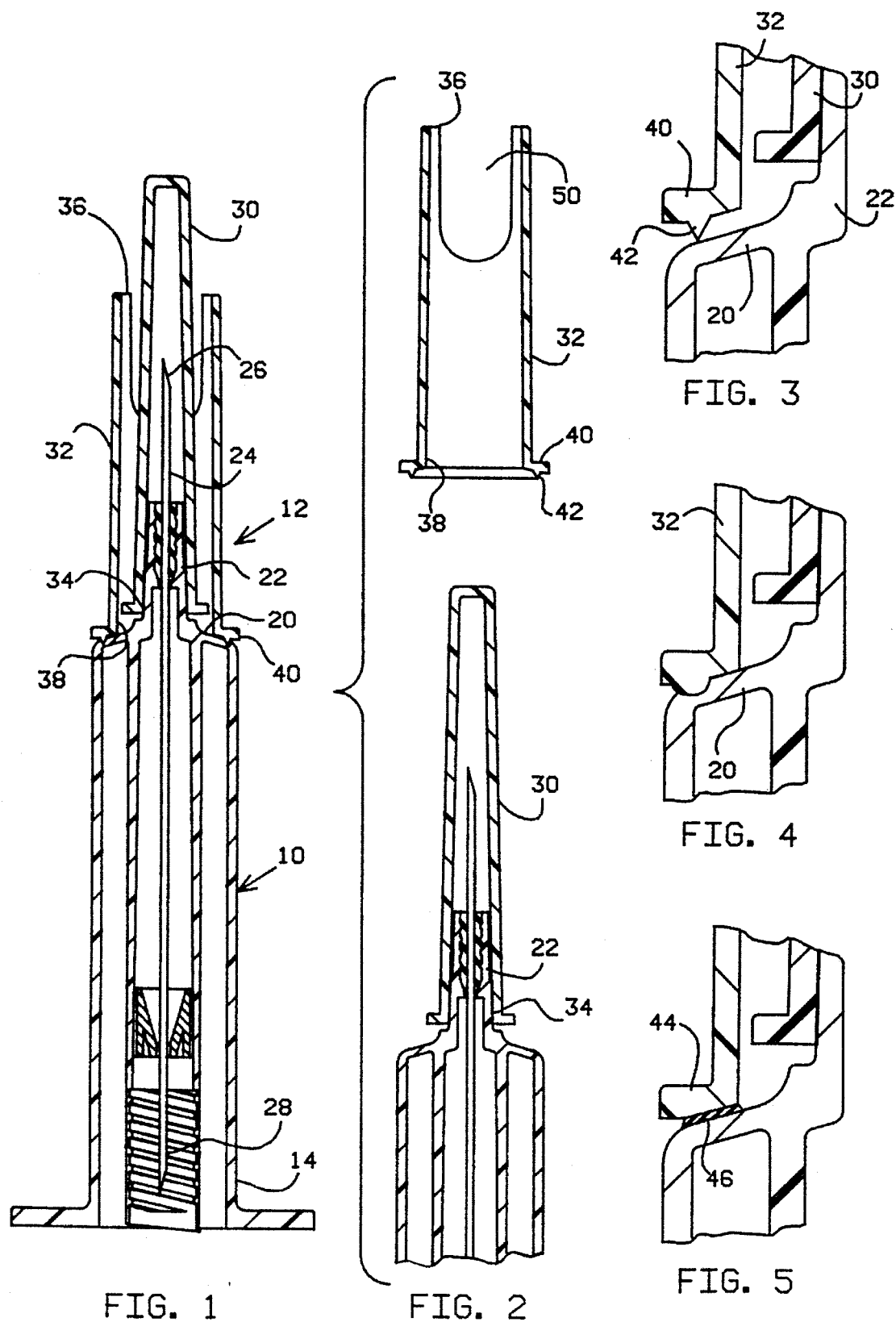

5,540,667

NEEDLE GUARD ASSEMBLY FOR SYRINGE

BACKGROUND OF THE INVENTION

This application is a continuation of U.S. patent application Ser. No. 08/276,880 filed Jul. 18, 1994 now abandoned which is a continuation of U.S. patent application Ser. No. 08/055,058 filed Apr. 19, 1993, now abandoned which is a continuation of U.S. patent application Ser. No. 07/765,356 filed Sep. 25, 1991, now abandoned.

This application is related to Ser. No. 07/600,556, filed Oct. 19, 1990 now U.S. Pat. No. 5,151,090.

The present invention relates to a prefilled emergency syringe and in particular to a needle guard assembly for a prefilled emergency syringe for use with an I.V. injection site.

The majority of fluids (drugs and other medical solutions) that are administered by emergency syringe are increasingly administered to patients through resealable injection sites connected to a patient intravenous access device such as a catheter or needle positioned within a vein of the patient. Fewer syringe injections are being made by a needle directly through the patient's skin (i.e. hypodermically).

One syringe that can be used either for a hypodermic injection or with an I.V. injection site is the Abboject® syringe sold by Abbott Laboratories. The Abboject syringe consists of a calibrated glass vial prefilled with a medical solution and a matching vial injector. The injector (or syringe housing) includes an integral syringe needle that can be used to inject the solution hypodermically into a patient or alternatively to inject the solution into an I.V. injection site connected to a patient. The syringe can be manufactured with the delivery needle enclosed by a removable needle hood to protect against needle stick prior to use and also to protect the sterile needle from contamination prior to use.

Healthcare providers are always at risk of accidental needle stick from syringe needles. Needles used for hypodermic injections pose the most publicized type of accidental needle stick due to the risk of infection from diseases such as AIDS and hepatitis. Thus there has been a proliferation of needle guards to protect against accidental needle stick from hypodermic type syringes.

Syringes that are used for fluid administration at I.V. injection sites also expose the healthcare provider to accidental needle stick. The risk may range from the side effects of drug residual on the needle to a life-threatening infection that may have infiltrated from the patient's blood system to the needle.

It is highly desirable to provide additional protection to the healthcare provider for accidental needle stick from syringes used only at I.V. injection sites as these type of syringes increasingly constitute the majority of sharp needles in the healthcare facility.

It is also desireable that the additional needle guard protection can be added to the standard Abboject syringes currently manufactured for both hypodermic and injection site injections, thus providing economy and flexibility in product manufacture.

One example of a protective sheath for a syringe needle is shown in U.S. Pat. No. 4,232,669 to Nitshke. Since the syringe is intended for use with an additive port of a flexible bag, the sheath of Nitshke does not extend beyond the needle point. The sheath and a removable cap protects and maintains the sterility of the syringe needle. However, the health care worker is exposed to potential needle stick when the cap is removed. The sheath of Nitshke is attached to the syringe by an collar engaging the needle hub. It therefore could not be added to the standard Abboject syringe without changing the current manufacturing process since the Abboject needle hood has a friction fit on the needle hub. Finally, although the Nitshke sheath is intended to protect the needle from breakage during use, the sheath is cantilevered and supported from the small diameter hub which is itself subject to breakage.

Another example of a protected needle is disclosed in U.S. Pat. No. 4,834,716 to Ogle. The protective sheath of Ogle in FIG. 2 is also fixed to the needle hub of the syringe. As previously discussed, fixing a protective sheath to the needle hub as disclosed by Ogle does not allow the Abboject needle hood to be attached to the hub as currently manufactured. Also the Ogle construction does not provide any additional structural support to protect the needle and hub from breaking.

It is therefore a primary object of the present invention to provide an improved needle guard to protect the healthcare provider from accidental needle stick from syringes used only at I.V. injection sites.

It is another object of the present invention to optionally add an additional needle guard protection to currently manufactured Abboject syringes so that the syringes may be more safely used at I.V. injection sites.

It is another object of the present invention to protect the sterilized needle from contamination until it is put in use.

It is another object of the present invention to provide solid support and connection to the syringe housing for the needle guard to protect the needle and needle hub from breaking.

SUMMARY OF THE INVENTION

The present invention is directed to a syringe that includes a needle guard mounted on the syringe housing.

The preferred embodiment of the invention includes a needle guard having a cylindrical sidewall abuttingly mounted to the front wall of the syringe and coaxially extending with the delivery needle. An annular clearance space is maintained between the needle hub and the interior of the cylindrical sidewall for the needle hood to be frictional fit on the hub, either before or after the sidewall is attached.

More particularly the needle guard includes a cylindrical sidewall which extends beyond the pointed end of the syringe needle. An annular flange extends radially from the needle guard sidewall for contact with the front wall of the syringe housing.

Specifically, an axially extending portion of the sidewall flange joins the needle guard sidewall to the housing by either a ultrasonic weld or a spin weld.

Other advantages and features of the present invention will become apparent from the following detailed description, the accompanying drawings and the appended claims.

BRIEF DESCRIPTION OF THE DRAWINGS

FIG. 1 is a cross section of the preferred embodiment of the present invention showing the syringe housing and needle guard assembly;

FIG. 2 is a cross section showing the needle guard sidewall prior to attachment to the syringe housing;

FIG. 3 is a detailed cross section showing a preferred construction of the sidewall flange prior to being welded to the syringe housing;

FIG. 4 is a detailed cross section of the needle guard after the sidewall is welded to the syringe housing; and FIG. 5 is a cross section of an alternative construction of the sidewall flange that is joined to the syringe housing.

DETAILED DESCRIPTION OF THE PREFERRED EMBODIMENT

FIG. 1 shows an embodiment of the present invention including a syringe housing 10 and a needle guard assembly 12 located at the forward end of the housing. The syringe housing 10 is an elongated hollow cylinder typically constructed of a molded plastic. The housing is open at the rear end 14. A removable cap (not shown) closes the rear end prior to use. Front wall portion 20 substantially closes the front end of the syringe housing. An integrally molded needle hub 22 extends forward from the front wall and secures a needle cannula 24 within the syringe housing. The needle 24 extends forward from the hub to a sharp front delivery point 26 and rearward to a sharp rear point 28.

A glass vial (not shown) is prefilled with a solution and sealed with a slidable stopper. The vial and stopper are engaged with the rear end 14 of the syringe housing such that the stopper is pierced by the rear needle point so as to provide fluid communication with the needle cannula 24.

The needle guard assembly 12 is positioned on the front wall portion 20 of the syringe housing coaxially with the delivery needle. The needle guard assembly 12 includes a needle hood 30 and a cylindrical sidewall 32. The hood member is a small diameter, closed-end hollow cylinder having internal dimensions adapted to cover the forward extending portion of needle 24. The open base end 34 of the hood is removably attached to the hub 22 with a circumferential friction fit. The friction fit between the hood and the needle hub includes a tortuous path construction so as to provide a sterile barrier to enclose the forward extending portion of the needle 24 within the hood.

The sidewall 32 is a separately molded hollow cylinder having a larger interior diameter than the exterior diameter of the hood 30 so that the sidewall fits over the hood. The forward open end 36 of the sidewall extends longitudinally forward beyond the front needle point 26 of the cannula. The open end 38 at the rear of the sidewall has a flange 40 that is constructed to circumferentially abut the front wall portion 20 of the syringe housing. The sidewall 32 can be mounted on the syringe housing 10 by various joining techniques that will presently be described.

In all the embodiments, the sidewall 32 is joined to the front wall 20 of the syringe housing with a radial clearance between the hub and the interior of the sidewall. The removable hood 30 occupies the annular clearance space that is maintained between the needle hub 22 and the interior of the cylindrical sidewall 32. The clearance space allows the hood 30 to be attached to the hub 22 prior to the sidewall being attached to the housing. Also the axially unobstructed clearance space allows the hood to be easily removed with the sidewall attached.

In the preferred embodiment of the present invention as best seen in FIGS. 3, an annular flange 40 extends radially from the rear end of the sidewall 32. The flange includes a circumferential, axially rearward extending portion 42. The extending portion 42 tapers to a point so as to function as an ultrasonic energy concentrator. During manufacture, the sidewall 32 can be positioned around the already assembled hood 30 such that the axially extending portion 42 is positioned in contact with the housing front wall 20. When a sonic energy horn is placed around the cylindrical sidewall 32 and energized, the axially extending portion 42 is welded into the front wall 20 of the syringe housing as shown in FIG. 4.

Alternatively, the same axially extending portion 42 allows the sidewall to be fused to the front wall 20 of the syringe housing by spin welding.

An alternate embodiment of the sidewall flange is shown by flange 44 in FIG. 5. This flange extends from the sidewall 32 substantially parallel to the front wall 20 of the housing so that it can be joined to the front wall by an adhesive bond at 46.

Each of the above alternatively joined embodiments allow a clearance between the needle hub 22 and the interior of the cylindrical sidewall 32 for the needle hood 30. In the current manufacturing process, a removable needle hood 30 is attached by a friction fit to the needle hub of substantially all Abboject syringes. For those Abboject syringes intended for use only at an I.V. injection site, the needle guard sidewall 32 can be added later as an additional step in the manufacturing process. Thus substantially all Abboject syringes, whether for use as a hypodermic or with a guarded needle at an injection site, can be initially manufactured with a friction fitted hood on the same production line.

The needle hood 30 permits the Abboject syringe needle of the present invention to be sterilized in a conventional manner, such as by ETO or radiation. The interior of the sidewall 32 does not need to be sterile. Therefore a cap is not needed to cover the open end of the sidewall. Furthermore, since the sidewall interior does not need to be sterile, the joint between the base of the sidewall 32 and the face of the housing 20 does not need to be a hermetic seal. The joint only needs to provide a strong and solid anchor for the sidewall to the face of the housing.

In the present invention, the joint is solidly supported by and anchored to the wall 20 of the housing rather than supported on the smaller diameter needle hub 22. The needle guard construction of the present invention provides additional protection for the hub and needle from breakage.

Initially the needle hood 30 covers and protects the needle 24 while the sidewall is being joined to the housing. It also provides a sterilizable enclosure for the needle and helps maintain the sterility of the needle until use.

The needle guard sidewall 32 includes two cutouts 50 positioned 180 degrees from each other at the open front end 36 of the sidewall. The depth of the cutouts accommodate different configurations of injection sites such as Y-sites.

It will be apparent from the foregoing description that the needle guard of the present invention not only protects the healthcare provider from inadvertent or accidental needle stick, but also provides additional advantages. Both the needle and the needle hub are protected from being broken during use since the sidewall is securely and permanently attached to the syringe housing. The removable needle hood protects the needle during manufacture and assembly and maintains the sterility of the needle after sterilization until the needle is used.

Although the present invention has been disclosed in terms of a preferred embodiment, it will be apparent to those skilled in the art that variations and modifications can be made without departing from the spirit and scope of the invention as defined in the following claims.

I claim:

1. A syringe having a needle guard assembly, said syringe having a syringe housing with a front wall substantially closing one end of said housing and a needle hub extending forward from said front wall securing a needle cannula, a forward extending needle portion of said needle cannula extending from said needle hub and terminating with a needle point, said needle guard assembly comprising:

a removable hood having an end covering said needle point and an open end having a friction fit with said needle hub to enclose said forward extending needle portion;

a cylindrical sidewall having a first and second open end, said first open end having an interior diameter dimensioned to fit over said removable hood, said second open end extending coaxially forward around said forward extending needle portion and beyond said needle point, said cylindrical sidewall having a rigid unitary construction from said first and to said second opens;

an annular flange extending radially outward forming said first open end of said cylindrical sidewall and substantially parallel to said front wall of said syringe housing, said annular flange having a rearward surface having means for bonding said first open end of said cylindrical sidewall to said front wall of said syringe housing so that an annular clearance space for said removable hood is maintained between said needle hub and said interior diameter of the cylindrical sidewall wherein said flange terminates at said front wall of said syringe.

2. A needle guard assembly of claim 1 further comprising a tortuous path at the friction fit between said removable hood and said needle hub so as to produce a sterile barrier for the enclosure around said extending needle portion.

3. A needle guard assembly of claim 1 wherein said bonding means comprises a sonic weld energy concentrator that extends axially rearward from said annular flange and is secured to said syringe housing by a sonic weld.

4. A needle guard assembly of claim 1 wherein said bonding means comprises a fusible portion that extends axially rearward from said annular flange and is secured to said syringe housing by a spin weld.

5. A needle guard assembly of claim 1 wherein said bonding means comprises an annular flange extending substantially parallel to said front wall of said syringe housing and is secured to said front wall by an adhesive bond.

6. A needle guard assembly of claim 1 wherein said first open end of said cylindrical sidewall has at least one cutout adapted to receive an inserted IV administration member.

7. A needle guard assembly of claim 1 wherein said first open end of said cylindrical sidewall has two oppositely disposed cutouts.

8. A method for assembling a needle guard including a removable needle hood and a cylindrical sidewall having a first and a second open end, to a syringe having a syringe housing with a front wall substantially closing one end of said syringe housing and a needle hub extending forward from said front wall securing a needle cannula, a portion of said needle cannula extending forward from said needle hub and terminating with a needle point, said removable needle hood having an end covering said needle point and an open end, said cylindrical sidewall having a rigid unitary construction from said first open end to said second open end, and said first open end formed by an annular flange extending radially outward having a rearward surface, comprising the steps of:

securing with a friction fit said open end of said removable needle hood to said needle hub to enclose said extending portion of said needle cannula; and coaxially and permanently bonding said first open end of said flange rearward surface to said front wall of said syringe housing so that an annular clearance space for said needle hood is maintained between said needle hub and an interior diameter of said cylindrical sidewall and said second open end of said cylindrical sidewall extends coaxially forward around said extending needle portion of said needle cannula and beyond said needle point, said flange terminates at said front wall of the syringe.

9. A method of claim 8 wherein said bonding is done by sonic welding.

10. A method of claim 8 wherein said bonding is done by spin welding.

11. A method of claim 8 wherein said bonding is done by adhesive bonding.

* * * * *